(12) United States Patent
Ueki et al.

(10) Patent No.: US 9,920,004 B2
(45) Date of Patent: Mar. 20, 2018

(54) METHOD FOR PRODUCING PHENOLIC COMPOUND

(71) Applicant: Sumitomo Chemical Company, Limited, Chuo-Ku, Tokyo (JP)

(72) Inventors: Kazuya Ueki, Takarazuka (JP); Toshiyuki Kiji, Takarazuka (JP); Hiroaki Okamoto, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/320,839

(22) PCT Filed: Jun. 9, 2015

(86) PCT No.: PCT/JP2015/066550
§ 371 (c)(1),
(2) Date: Dec. 21, 2016

(87) PCT Pub. No.: WO2015/198850
PCT Pub. Date: Dec. 30, 2015

(65) Prior Publication Data
US 2017/0137377 A1   May 18, 2017

(30) Foreign Application Priority Data
Jun. 26, 2014   (JP) .................................. 2014-131040

(51) Int. Cl.
*C07C 315/04*   (2006.01)
*C07C 315/02*   (2006.01)

(52) U.S. Cl.
CPC .......... *C07C 315/04* (2013.01); *C07C 315/02* (2013.01)

(58) Field of Classification Search
None
See application file for complete search history.

(56) References Cited

U.S. PATENT DOCUMENTS

| 5,028,711 A | 7/1991 | Stenzel et al. |
| 2004/0110775 A1 | 6/2004 | Griffin et al. |
| 2011/0105461 A1 | 5/2011 | Sonesson et al. |
| 2012/0232281 A1 | 9/2012 | Castellin et al. |
| 2014/0170855 A1 | 6/2014 | Nakajima et al. |
| 2014/0194290 A1 | 7/2014 | Takahashi et al. |
| 2015/0313234 A1 | 11/2015 | Takahashi et al. |

FOREIGN PATENT DOCUMENTS

| CA | 2102904 A1 | 11/1992 |
| CN | 103360316 A | 10/2013 |
| DE | 3836149 A1 | 5/1990 |
| JP | 55094126 A | 7/1975 |
| JP | H0272171 A | 3/1990 |
| JP | H06508109 A | 9/1994 |
| JP | H0782267 A | 3/1995 |
| JP | 2004517930 A | 6/2004 |
| JP | 2012188414 A | 10/2012 |
| JP | 2013532187 A | 8/2013 |
| WO | 2009133107 A1 | 11/2009 |
| WO | 2012007938 A1 | 1/2012 |
| WO | 2013018928 A1 | 2/2013 |
| WO | 2013022099 A1 | 2/2013 |
| WO | 2014104407 A1 | 7/2014 |

OTHER PUBLICATIONS

Trost, B, Acc. Chem. Res. 2002, 35, 695-705.*
Int'l Search Report dated Jul. 14, 2015 in Int'l Application No. PCT/JP2015/066550 (English Translation).
Int'l Preliminary Report on Patentability dated Dec. 27, 2016 in Int'l Application No. PCT/JP2015/066550 (English ranslation).
Umemoto et al, "Effective Methods for Preparing S-(Trifluoromethyl) Dibenzothiophenium Salts," Journal of Flourine Chemistry, vol. 98, pp. 75-81 (1999).

* cited by examiner

*Primary Examiner* — Clinton Brooks
(74) *Attorney, Agent, or Firm* — Panitch Schwarze Belisario & Nadel LLP

(57) ABSTRACT

Provided is a method for producing a compound represented by formula (2-b), which is useful as an intermediate for producing agricultural chemicals. The method includes a step for obtaining a compound represented by formula (2-a) by oxidizing the compound represented by formula (1) with hydrogen peroxide in the presence of sulfuric acid and/or a $C_{1-6}$ alkanesulfonic acid that may be halogen-substituted and in the presence of a $C_{2-12}$ aliphatic carboxylic acid and/or sulfolane. The method also includes a step for obtaining a compound represented by formula (2-b) by nitrating a compound represented by formula (2-a) in the presence of sulfuric acid and/or a $C_{1-6}$ alkanesulfonic acid that may be halogen-substituted.

3 Claims, No Drawings

METHOD FOR PRODUCING PHENOLIC COMPOUND

CROSS-REFERENCE TO RELATED APPLICATION

This application is a Section 371 of International Application No. PCT/JP2015/066550, filed Jun. 9, 2015, which was published in the Japanese language on Dec. 30, 2015, under International Publication No. WO 2015/198850 A1, and the disclosure of which is incorporated herein by reference.

TECHNICAL FIELD

The present invention relates to a method for producing 4-(trifluoromethylsulfinyl)phenol or 4-(trifluoromethylsulfonyl)phenol having a nitro group or an amino group at the 2-position.

BACKGROUND ART 4-(Trifluoromethylsulfinyl)phenol or 4-(trifluoromethylsulfonyl)phenol having a nitro group or an amino group at the 2-position is an important compound as a production intermediate of agrochemical (for example, refer to Production process 17 of WO2013/018928).

A method of oxidizing 4-(trifluoromethylsulfanyl)phenol using a sodium tungstate catalyst is known in WO2009/133107.

SUMMARY OF THE INVENTION

The present invention provides a method for producing 4-(trifluoromethylsulfinyl)phenol and 4-(trifluoromethylsulfonyl)phenol having a nitro group or an amino group at the 2-position.

According to the present invention, 4-(trifluoromethylsulfonyl)phenol or 4-(trifluoromethylsulfanyl)phenol obtained by oxidizing 4-(trifluoromethylsulfanyl)phenol with hydrogen peroxide, in the presence of at least one acid selected from Group I consisting of sulfuric acid and C1 to C6 alkanesulfonic acids optionally substituted with halogen and at least one compound selected from Group II consisting of C2 to C12 aliphatic carboxylic acids and sulfolane is nitrated, whereby 4-(triflouromethylsulfinyl)phenol and 4-(trifluoromethylsulfonyl)phenol having a nitro group at the 2-position can be produced. In addition, a reduction reaction is further performed, in the presence of a heterogeneous transition metal catalyst, whereby 4-(trifluoromethylsulfinyl)phenol and 4-(trifluoromethylsulfonyl)phenol having an amino group at the 2-position can be produced.

The present invention is a method for producing a compound represented by formula (2-b) (hereinafter, referred to as compound (2-b)):

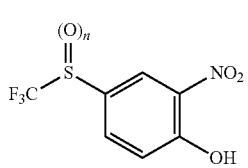

wherein n represents 1 or 2, the method comprising:
step A of obtaining a compound represented by formula (2-a) (hereinafter, referred to as compound (2-a)):

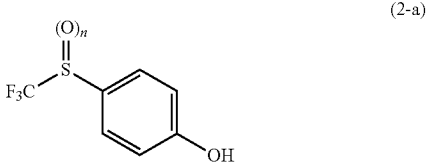

wherein n has the same meaning as described above, by oxidizing a compound represented by formula (1) (hereinafter, referred to as compound (1)):

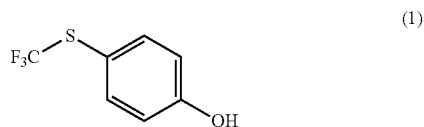 [SMILES: Oc1ccc(SC(F)(F)F)cc1]

with hydrogen peroxide, in the presence of at least one acid selected from Group I consisting of sulfuric acid and C1 to C6 alkanesulfonic acids optionally substituted with halogen and at least one compound selected from Group II consisting of C2 to C12 aliphatic carboxylic acids and sulfolane (hereinafter, referred to as step A); and step B of obtaining compound (2-b) by nitrating the compound (2-a) obtained in step A, in the presence of at least one acid selected from Group I consisting of sulfuric acid and C1 to C6 alkanesulfonic acids optionally substituted with halogen (hereinafter, referred to as step B).

In addition, the present invention is a method for producing a compound represented by formula (2-c) (hereinafter, referred to as compound (2-c)):

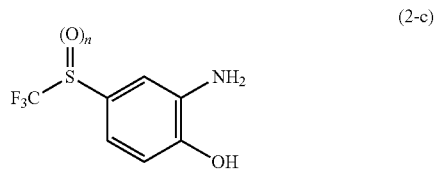

wherein n has the same meaning as described above, the method comprising:

step A of obtaining compound (2-a) by oxidizing compound (1) with hydrogen peroxide, in the presence of at least one acid selected from Group I consisting of sulfuric acid and C1 to C6 alkanesulfonic acids optionally substituted with halogen and at least one compound selected from Group II consisting of C2 to C12 aliphatic carboxylic acids and sulfolane;

step B of obtaining compound (2-b) by nitrating the compound (2-a) obtained in step A, in the presence of at least one acid selected from Group I consisting of sulfuric acid and C1 to C6 alkanesulfonic acids optionally substituted with halogen; and step C of obtaining compound (2-c) by reducing the compound (2-b) obtained in step B, in the presence of a heterogeneous transition metal catalyst (hereinafter, referred to as step C).

MODE FOR CARRYING OUT THE INVENTION

Hereinbelow, the present invention will be described in detail.

First, step A will be described.

Compound (1), i.e., 4-(trifluoromethylsulfanyl)phenol is oxidized with hydrogen peroxide, in the presence of at least one acid selected from Group I consisting of sulfuric acid and C1 to C6 alkanesulfonic acids optionally substituted with halogen (hereinafter, referred, to as acid I) and at least one compound selected from Group II consisting of C2 to C12 aliphatic carboxylic acids and sulfolane (hereinafter, referred to as compound II).

Examples of the C1 to C6 alkanesulfonic acids optionally substituted with halogen include methanesulfonic acid, ethanesulfonic acid, propanesulfonic acid, trifluoromethanesulfonic acid, and the like; and methanesulfonic acid and ethanesulfonic acid are preferred.

Acid I is preferably a sulfonic acid that is easily available.

The use amount of acid I is usually 0.1 to 20 times and preferably 0.5 to 5 times per weight of compound (1).

Hydrogen peroxide is used as an aqueous solution, and the concentration thereof is usually 10 to 70% by weight and preferably 30 to 60% by weight.

The use amount of hydrogen peroxide when producing compound (2-a) wherein n is 1 is usually 0.8 to 2.5 times and preferably 0.9 to 1.3 times per mole of compound (1). The use amount of hydrogen peroxide when producing compound (2-a) wherein n is 2 is usually 1.8 to 5 times and preferably 1.9 to 2.5 times per mole of compound (1).

The reaction in step A is performed in the presence of compound II, in order to improve solubility of all raw materials and reaction products.

Examples of the C2 to C12 aliphatic carboxylic acid include acetic acid, propionic acid, butyric acid, hexanoic acid, octanoic acid, 2-ethylhexanoic acid, decanoic acid, dodecanoic acid, and the like; and hexanoic acid, octanoic acid and 2-ethylhexanoic acid are more preferred, and 2-ethylhexanoic acid that is easily available is further preferred.

The use amount of compound II is usually 0.1 to 5.0 times and preferably 0.5 to 2.0 times per weight of compound (1).

As mixing order of compound (1), acid I, compound II and hydrogen peroxide, it is preferred to add hydrogen peroxide at last, and specific examples of the mixing order include a method of mixing compound (1), acid I and compound II, and then adding hydrogen peroxide; a method of mixing compound (1), a part of acid I and compound II and then adding remaining acid I and hydrogen peroxide to the mixture at the same time; and the like.

The reaction temperature when producing compound (2-a) wherein n is 1 is 0 to 60° C. and preferably 5 to 40° C.

The reaction temperature when producing compound (2-a) wherein n is 2 is 50 to 100° C. and preferably 60 to 80° C. The reaction time varies also depending on the reaction temperature, but is usually each 1 to 50 hours or so.

After completion of the reaction, the reaction mixture is diluted with water, and compound (2-a) can be isolated by organic solvent extraction, separation by filtration of the precipitated solid, or the like. Also, the isolated compound (2-a) can be further purified by recrystallization and chromatography.

The compound (2-a) is 4-(trifluoromethylsulfinyl)phenol or 4-(trifluoromethylsulfonyl)phenol.

Next, step B will be described.

Nitration reaction of the compound (2-a) is usually performed by mixing with nitric acid in the presence of acid I.

Also, it is preferred to mix with nitric acid without isolating the compound (2-a) obtained in step A, in terms of production efficiency. Specific examples of nitric acid to be used include 60 to 98% by weight nitric acid and fuming nitric acid.

Mixing order of compound (2-a), nitric acid and acid I is not particularly limited, and usually, nitric acid is added to a mixture of compound (2-a) and acid I. Also, the nitration reaction may be performed in the presence of compound II, and when compound II is used, examples of the mixing order include a method of adding nitric acid to a mixture of compound (2-a), acid I and compound II.

When step B is performed without isolating the compound (2-a) obtained in step A, removal of water from the reaction mixture of step A by operation such as liquid separation, and addition of acid I are performed, as necessary.

The use amount of nitric acid is usually 0.8 to 3.0 times and preferably 0.9 to 1.9 times per mole of compound (2-a).

The reaction temperature is usually 0 to 100° C. and preferably 5 to 50° C. The reaction time varies also depending on the reaction temperature, but is usually 1 to 50 hours.

After completion of the reaction, the reaction mixture is diluted with water, and compound (2-b) can be isolated by organic solvent extraction, filtration of the precipitated solid, or the like. Also, the isolated compound (2-b) can be further purified by recrystallization and chromatography.

The compound (2-b) is 4-(trifluoromethylsulfinyl)-2-nitrophenol or 4-(trifluoromethylsulfonyl)-2-nitrophenol.

Next, step C will be described.

Step C is performed by reacting compound (2-b) with hydrogen in the presence of a heterogeneous transition metal catalyst. The heterogeneous transition metal catalyst is inactivated by a compound having a sulfanyl group, thus it is preferred to carry out step C subsequent to steps A and B.

Specific examples of the heterogeneous transition metal catalyst include Raney catalysts such as Raney nickel and Raney cobalt; and heterogeneous platinum-group catalysts such as palladium/carbon, palladium/silica, palladium/alumina, platinum/carbon, platinum/silica, platinum/alumina, rhodium/carbon, rhodium/silica, rhodium/alumina, iridium/carbon, iridium/silica, and iridium/alumina.

Heterogeneous platinum-group catalysts of palladium, platinum, ruthenium, rhodium, iridium and osmium that belong to platinum-group elements are preferred, heterogeneous platinum catalysts are further preferred in an industrial production method, and platinum/carbon is most preferred.

The use amount of the heterogeneous transition metal catalyst is usually 0.01 to 1.0% by mol and preferably 0.05 to 0.5% by mol based on compound (2-b).

Step C is performed in a solvent, and examples of the solvent include alcohol solvents such as methanol, ethanol, propanol, 2-propanol and butanol; aromatic hydrocarbon solvents such as toluene, xylene and ethyl benzene; aliphatic hydrocarbon solvents such as hexane and heptane; aliphatic halogenated hydrocarbon solvents such, as dichloromethane and 1,2-dichloroethane; ether solvents such as diethyl ether, tetrahydrofuran and methyl tert-butyl ether; ester solvents such as ethyl acetate and butyl acetate; and the like and water, and these solvents may be used alone or as a mixture.

Mixing order of compound (2-b), heterogeneous transition metal catalyst, solvent and hydrogen is not particularly limited, and usually, examples of the mixing order include a method of adding hydrogen to a mixture of compound (2-b), solvent and heterogeneous transition metal catalyst; and a method of each adding compound (2-b) and hydrogen to a mixture of solvent and heterogeneous transition metal catalyst.

The partial pressure of hydrogen used in the reaction is usually 0.01 to 5 MPa and preferably 0.05 to 1 MPa.

The reaction temperature is usually 0 to 100° C. and preferably 10 to 50° C.

The reaction time varies depending on the partial pressure of hydrogen and the reaction temperature, but is usually 1 to 50 hours.

After completion of the reaction, the heterogeneous transition metal catalyst is separated by filtration, and the resulting filtrate is concentrated, extracted with an organic solvent, and subjected to crystallization or the like, whereby compound (2-c) can be obtained. Also, the isolated compound (2-c) can be further purified by recrystallization and chromatography.

The compound (2-c) is 4-(trifluoromethylsulfinyl)-2-aminophenol or 4-(trifluoromethylsulfonyl)-2-aminophenol.

EXAMPLES

Hereinbelow, the present invention will be specifically described with reference to examples. However, the present invention is not limited only to these examples.

Example 1

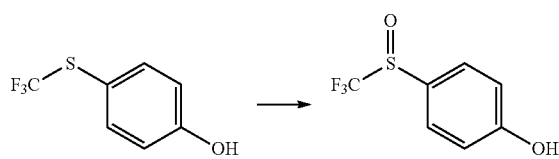 [SMILES: Oc1ccc(SC(F)(F)F)cc1 ; O=S(c1ccc(O)cc1)C(F)(F)F]

To a mixture of 25.0 g of 4-(trifluoromethylsulfanyl) phenol, 39.5 g of 96 wt % sulfuric acid and 25.0 g of 2-ethylhexanoic acid was added drop wise 12.6 g of 35 wt % hydrogen peroxide at 10° C. over 1 hour, and the resulting mixture was stirred for 1 hour. To the reaction mixture were added 22.1 g of a 28 wt % aqueous sodium hydroxide solution, 1.7 g of a 22 wt % aqueous sodium sulfite solution, 50 g of water and 50 g of hexane, and the precipitated solid was filtered at 0° C. The solid was washed with water and hexane and dried to obtain 24.8 g (content of 99.7 wt %) of 4-(trifluoromethylsulfinyl)phenol.

Example 2

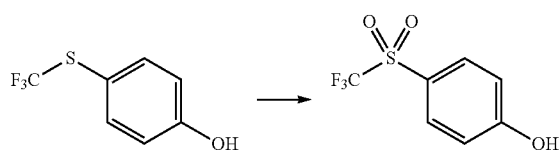 [SMILES: Oc1ccc(SC(F)(F)F)cc1 ; O=S(=O)(c1ccc(O)cc1)C(F)(F)F]

To a mixture of 100.0 g of 4-(trifluoromethylsulfanyl) phenol, 158.0 g of 96 wt % sulfuric acid and 99.8 g of 2-ethylhexanoic acid was added dropwise 49.8 g of 35 wt % hydrogen peroxide at 10° C. over 4 hours. Further, 69.72 g of 35 wt % hydrogen peroxide was added dropwise thereto at 70° C. over 4 hours, and the resulting mixture was stirred for 0.5 hours. When the reaction mixture was separated, and the organic layer (212.4 g) was analyzed by a liquid chromatography, (trifluoromethylsulfonyl)phenol was contained in an amount of 52.3 wt %. To 42.7 g of the organic layer was added 80 g of hexane, and the precipitated solid was filtered at 25° C. The resulting solid was washed with water and hexane and then dried to obtain 19.1 g (content of 99.0 wt %) of 4-(trifluoromethylsulfonyl)phenol.

Example 3

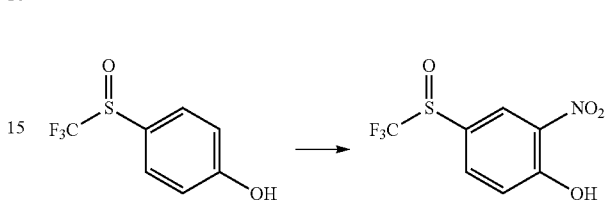

To a mixture of 1.0 g of 4-(trifluoromethylsulfinyl)phenol, 1.6 g of 96 wt % sulfuric acid and 1.0 g of 2-ethylhexanoic acid was added dropwise 0.7 g of 60 wt % nitric acid at 30 to 40° C. over 1.5 hours, and the resulting mixture was stirred at 40° C. for 0.5 hours. The reaction mixture was neutralized by adding an aqueous sodium hydroxide solution, and extracted using ethyl acetate to obtain 31.1 g (content of 3.7 wt %) of a solution containing 4-(trifluoromethylsulfinyl)-2-nitrophenol.

Example 4

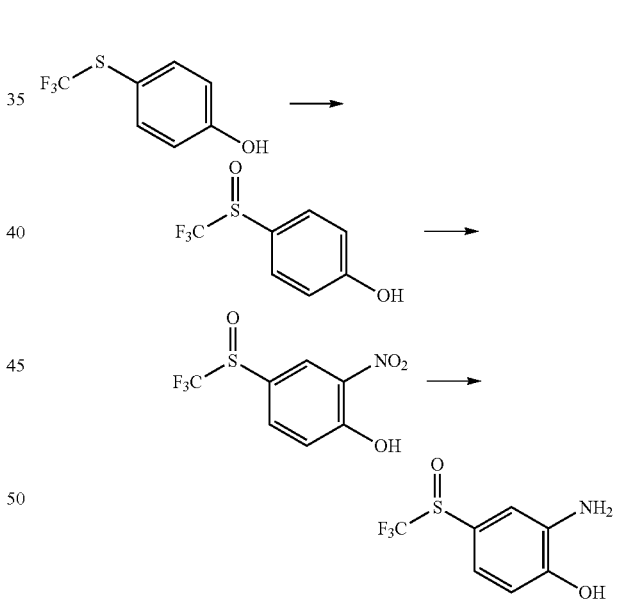

To a mixture of 125.0 g of 4-(trifluoromethylsulfanyl) phenol, 39.0 g of 96 wt % sulfuric acid and 125.0 g of 2-ethylhexanoic acid were added dropwise 63.0 g of 35 wt % hydrogen peroxide and 156.0 g of 96 wt % sulfuric acid at the same time at 20 to 40° C. over 1.5 hours, and the resulting mixture was stirred for 2 hours. Subsequently, 171.0 g of 96 wt % sulfuric acid was added to the reaction mixture, and 63.1 g of 70 wt % nitric acid was added dropwise thereto at 30° C. over 2 hours. To the reaction mixture were added 205.0 g of a 28 wt % aqueous sodium hydroxide solution, 100.0 g of a 22 wt % aqueous sodium sulfite solution, 100.0 g of water and 124.0 g of toluene, and the resulting mixture was dissolved by heating at 70° C., then the aqueous layer was removed. The resulting organic layer was washed by adding 124.0 g of toluene and 124.0 g of water to obtain 541.4 g of an organic layer. Then, 173.6 g among 541.4 g of the resulting organic layer was concentrated and cooled to 0° C. over 15 hours, and the precipitated solid was filtered. The resulting solid was sequentially washed with 100.0 g of water and 100.0 g of hexane and then dried to obtain 45.5 g (content of 99.7 wt %) of 4-(trifluoromethylsulfinyl)-2-nitrophenol.

To a mixture of 1.4 g of the resulting 4-(trifluoromethylsulfinyl)-2-nitrophenol, 1.4 g of 2-propanol and 4.2 g of methanol was added 0.2 g of platinum/carbon (platinum carrying amount of 3 wt %, water content rate of 50 wt %), and the resulting mixture was stirred at 40° C. for 8 hours in a hydrogen atmosphere. The platinum/carbon was filtered off from the reaction mixture, and the filtrate was concentrated to obtain 1.2 g (content of 98.8 wt %) of 4-(trifluoromethylsulfinyl)-2-aminophenol.

Also 55.3 g of toluene was distilled off from 131.9 g among 541.4 g of the above organic layer by concentration under reduced pressure. To this concentrate were added 114.0 g of methanol and subsequently 2.3 g of platinum/carbon (platinum carrying amount of 3 wt %, water content rats of 61 wt %), and the resulting mixture was stirred at 40° C. for 3 hours in a hydrogen atmosphere (partial pressure of hydrogen: 0.8 MPa). The platinum/carbon was filtered off from the reaction mixture, and also the platinum/carbon was washed with methanol. The filtrate and the washing liquid were combined to obtain 215.6 g of a solution containing 4-(trifluoromethylsulfinyl)-2-aminophenol (content of 13.9 wt %).

Example 5

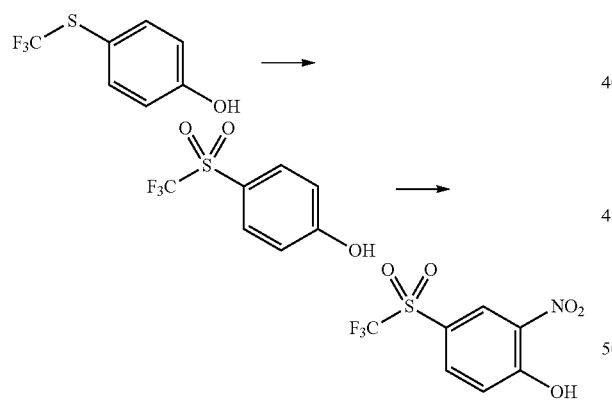

To a mixture of 10.0 g of 4-(trifluoromethylsulfanyl) phenol, 15.8 g of 96 wt % sulfuric acid and 10.0 g of 2-ethylhexanoic acid was added dropwise 6.1 g of 35 wt % hydrogen peroxide at 20° C. or lower over 1 hour. Subsequently, 4.8 g of 35 wt % hydrogen peroxide was added thereto at 65 to 82° C. over 4 hours, and the resulting mixture was stirred for 5 hours. The reaction mixture was separated, and 2.5 g of 96 wt % sulfuric acid was added to the organic layer, subsequently 8.9 g of 60 wt % nitric acid was added thereto at 50 to 70° C. After stirring the resulting mixture at 50 to 70° C. for 9 hours, the reaction mixture was cooled to room temperature, and separated. To the organic layer was added 10.0 g of heptane, and the mixture was cooled to 3° C. over 4 hours, then the precipitated solid was filtered. The resulting solid was washed with 10.0 g of hexane and dried to obtain 12.3 g (content of 87.7 wt %) of 4-(trifluoromethylsulfonyl)-2-nitrophenol.

Example 6

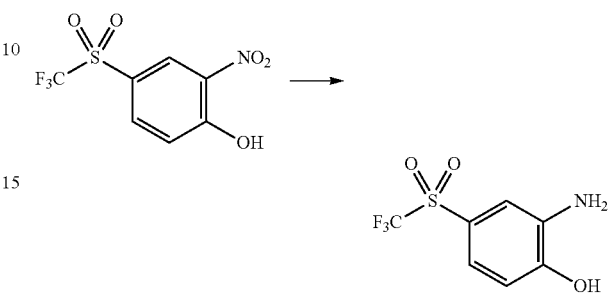

To a mixture (5.4 g, content of 55.8%) of 4-(trifluoromethylsulfonyl)-2-nitrophenol and 2-ethylhexanoic acid were added 16.2 g of methanol and subsequently 0.18 g of platinum/carbon (platinum carrying amount of 3%, water content of 61%), and the resulting mixture was stirred at 40° C. for 13 hours in a hydrogen atmosphere. The platinum/carbon was filtered off from the reaction mixture, and also the platinum/carbon was washed with methanol. The filtrate and the washing liquid were combined and concentrated to obtain 4.9 g of 4-(trifluoromethylsulfonyl)-2-aminophenol (content of 49.7%).

Example 7

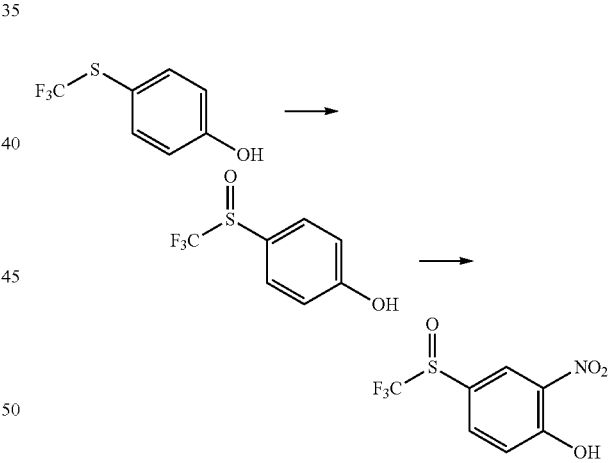

To a mixture of 60.0 g of 4-(trifluoromethylsulfanyl) phenol, 94.7 g of 80 wt % sulfuric acid and 60.0 g of sulfolane was added dropwise 30.3 g of 35 wt % hydrogen peroxide at 50 to 60° C. over 4.5 hours. After termination of the dropwise addition, the mixture was stirred at 75° C. for 1 hour to obtain 242.4 g of a reaction mixture containing 4-(trifluoromethylsulfinyl)phenol (confirmed by a liquid chromatography). To 63.3 g among 242.4 g of the reaction mixture was added dropwise 12.6 g of 65 wt % nitric acid at 60 to 70° C. over 2 hours. Thereto was added 15.6 g of water, and the mixture was heated to 74° C., then the aqueous layer was removed by liquid separation. To the organic layer was added 16.0 g of toluene, and the mixture was cooled to 2° C. over 2 hours, then the precipitated solid was separated by filtration. The resulting solid was washed with 15.0 g of toluene cooled to 0° C. and dried to obtain 11.1 g (content of 95.0 wt %) of 4-(trifluoromethylsulfinyl)-2-nitrophenol.

Example 8

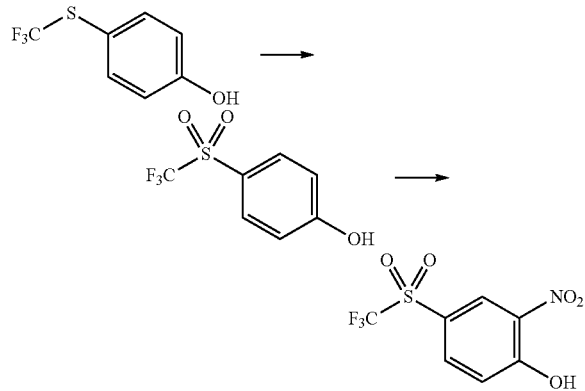

To a mixture of 10.0 g of 4-(trifluoromethylsulfanyl)phenol, 15.8 g of 80 wt % sulfuric acid and 10.0 g of sulfolane was added dropwise 12.0 g of 35 wt % hydrogen peroxide at 60 to 70° C. over 4 hours, then the mixture was stirred at the same temperature for 4 hours. The reaction mixture was heated to 90° C., and 8.6 g of 60 wt % nitric acid was added dropwise thereto at 90° C. over 2 hours, then the mixture was stirred at the same temperature for 3 hours. The reaction mixture was extracted with 10.0 g of toluene to obtain 33.2 g (content of 30.3 wt %) of a solution containing 4-(trifluoromethylsulfonyl)-2-nitrophenol.

Example 9

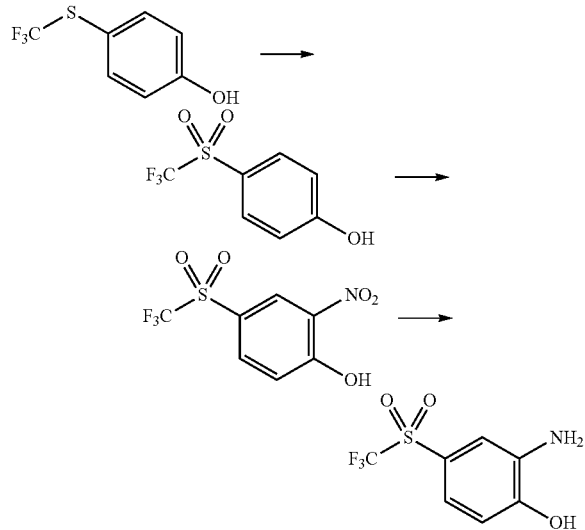

To a mixture of 100.0 g of 4-(trifluoromethylsulfanyl)phenol, 158.0 g of 96% sulfuric acid and 99.8 g of 2-ethylhexanoic acid was added dropwise 49.8 g of 35 wt % hydrogen peroxide at 10° C. over 4 hours. Thereafter, the mixture was heated to 70° C., subsequently, 69.72 g of 35 wt % hydrogen peroxide was added dropwise thereto at 70° C. over 4 hours, and the resulting mixture was stirred for 30 minutes. The reaction mixture was separated to obtain 212.4 g of an organic layer containing (content of 52.3 wt %) 4-(trifluoromethylsulfonyl)phenol. To 160.2 g among 212.4 g of the organic layer was added 225.9 g of 96 wt % sulfuric acid, and 38.2 g of 70 wt % nitric acid was added dropwise thereto at 30° C. over 4 hours, then the mixture was stirred for 1 hour. To the reaction mixture was added 75.0 g of water, and an organic layer obtained by liquid separation was washed with 75.0 g of water to obtain 166.8 g of an organic layer containing (content of 55.8 wt %) 4-(trifluoromethylsulfonyl)-2-nitrophenol. To 54.9 g among 166.8 g of the resulting organic layer were added 85.1 g of methanol and subsequently 0.9 g of platinum/carbon (platinum carrying amount of 3 wt %, water content of 61 wt %), and the resulting mixture was stirred at 40° C. for 5 hours in a hydrogen atmosphere (partial pressure of hydrogen: 0.6 MPa). The platinum/carbon was filtered off from the reaction mixture, and also the platinum/carbon was washed with methanol. The filtrate and the washing liquid were combined to obtain 168.8 g of a solution containing 4-(trifluoromethylsulfonyl)-2-aminophenol (content of 15.4 wt %).

Example 10

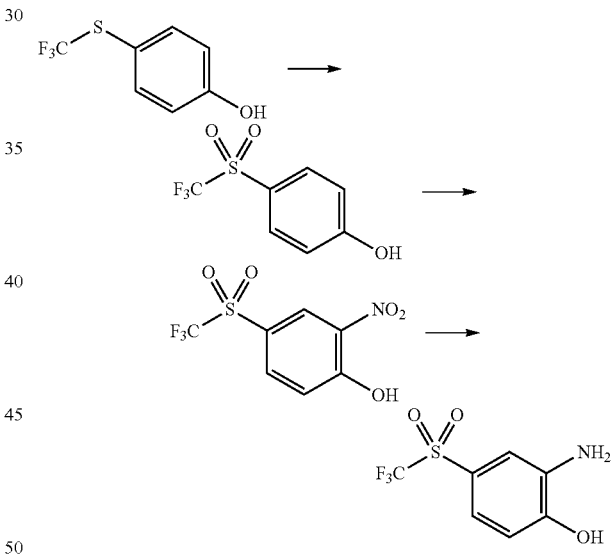

To a mixture of 100.0 g of 4-(trifluoromethylsulfanyl)phenol, 158.0 g of 96% sulfuric acid and 99.8 g of 2-ethylhexanoic acid was added dropwise 49.8 g of 35 wt % hydrogen peroxide at 10° C. over 4 hours. Thereafter, the mixture was heated to 70° C., subsequently, 69.7 g of 35 wt % hydrogen peroxide was added dropwise thereto at 70° C. over 4 hours, and the resulting mixture was stirred for 30 minutes. The reaction mixture was separated to obtain 212.4 g of an organic layer containing (content of 52.3 wt %) 4-(trifluoromethylsulfonyl)phenol. To 160.2 g among 212.4 g of the organic layer was added 225.9 g of 96 wt % sulfuric acid, and 38.2 g of 70 wt % nitric acid was added dropwise thereto at 30° C. over 4 hours, then the mixture was stirred for 1 hour. To the reaction mixture was added 75.0 g of water, and an organic layer obtained by liquid separation was washed with 75.0 g of water to obtain 166.8 g of an organic layer containing (content of 55.8 wt %) 4-(trifluoromethylsulfonyl)-2-nitrophenol. To 11.4 g of the resulting organic layer were added 19.1 g of methanol and subsequently 0.1 g of platinum/carbon (platinum carrying amount of 3 wt %, water content of 61 wt %), and the resulting mixture was stirred at 40° C. for 7 hours in a hydrogen atmosphere (partial pressure of hydrogen: 0.5 MPa). Thereafter, 0.1 g of platinum/carbon (platinum carrying amount of 3 wt %, water content of 61 wt %) was further added thereto, and the resulting mixture was stirred for 4 hours in a hydrogen atmosphere (partial pressure of hydrogen: 0.5 MPa). The platinum/carbon was filtered off from the reaction mixture, and also the platinum/carbon was washed with methanol. The filtrate and the washing liquid were combined to obtain 43.2 g of a solution containing 4-(trifluoromethylsulfonyl)-2-aminophenol (content of 12.9 wt %). Then, 40.0 g of the resulting solution was concentrated under reduced pressure, and 10.4 g of xylene was added to the residue, then the mixture was further concentrated under reduced pressure. The resulting xylene solution was heated to 80° C., and 3.9 g of heptane was added thereto. The mixture was kept warm for 1 hour and then cooled to 0° C. over 16 hours, and the precipitated solid was filtered. The resulting solid was washed with 9.1 g of xylene cooled to 0° C. and dried to obtain 4.7 g (content of 97.5 wt %) of 4-(trifluoromethylsulfonyl)-2-aminophenol.

Example 11

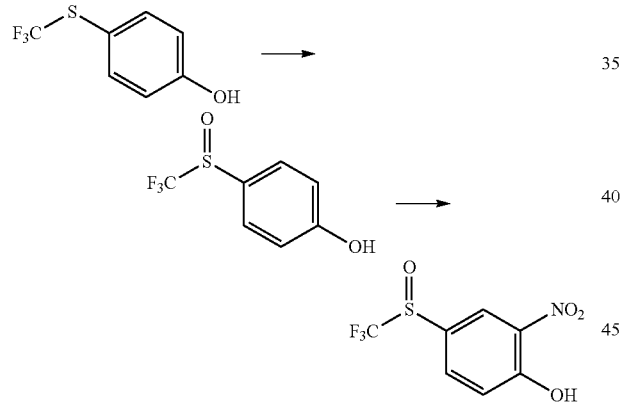

To a mixture of 20.0 g of 4-(trifluoromethylsulfanyl) phenol, 6.3 g of 96 wt % sulfuric acid and 20.0 g of 2-ethylhexanoic acid were added dropwise 5.87 g of 60 wt % hydrogen peroxide and 25.3 g of 96 wt % sulfuric acid at the same time at 20° C. over 3 hours, and the resulting mixture was stirred for 30 minutes. Subsequently, 6.6 g of 98 wt % nitric acid was added dropwise to the reaction mixture at 20° C. over 4 hours, and the mixture was stirred for 30 minutes. Thereto was further added 1.3 g of 98 wt % nitric acid, and the mixture was stirred for 1 hour. The reaction mixture was neutralized by adding 10 g of water and 17.7 g of a 28 wt % aqueous sodium hydroxide solution thereto, and was extracted with 14.0 g of xylene. The organic layer was washed by adding 16.0 g of xylene, 20 g of water and 5.9 g of a 23% aqueous sodium sulfite solution, and separated to obtain 72.2 g (content of 32.2 wt %) of an organic layer containing 4-(trifluoromethylsulfinyl)-2-nitrophenol.

INDUSTRIAL APPLICABILITY

The method of the present invention can produce compound (2-b) and compound (2-c) useful as production intermediates of agrochemicals.

The invention claimed is:
1. A method for producing a compound of formula (2-b):

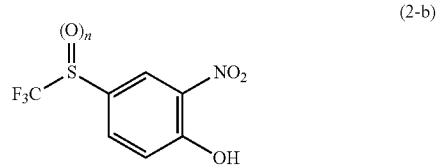

wherein n represents 1 or 2, the method comprising:
step A of obtaining a compound of formula (2-a):

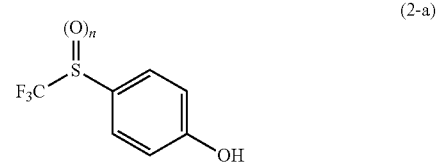

wherein n has the same meaning as described above, by oxidizing a compound of formula (1):

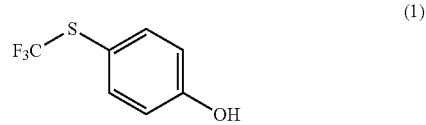 [SMILES: Oc1ccc(SC(F)(F)F)cc1]

with hydrogen peroxide in the presence of sulfuric acid and 2-ethylhexanoic acid; and
step B of obtaining a compound of formula (2-b) by nitrating the compound of formula (2-a) obtained in step A in the presence of at least one acid selected from Group I consisting of sulfuric acid and C1 to C6 alkanesulfonic acids optionally substituted with halogen;
wherein the compound of formula (2-a) obtained in step A is subjected to step B without isolation.

2. A method for producing a compound of formula (2-c):

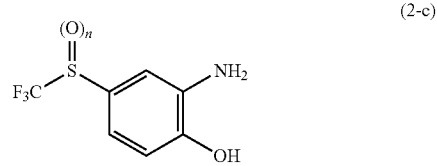

wherein n represents 1 or 2, the method comprising:

step A of obtaining a compound of formula (2-a):

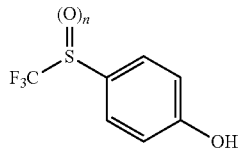

(2-a)

wherein n has the same meaning as described above, by oxidizing a compound of formula (1):

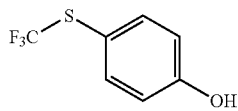

(1)

with hydrogen peroxide in the presence of sulfuric acid and 2-ethylhexanoic acid;

step B of obtaining a compound of formula (2-b):

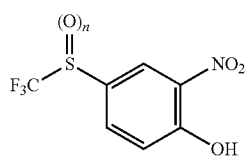

(2-b)

wherein n has the same meaning as described above,
by nitrating the compound of formula (2-a) obtained in step A in the presence of at least one acid selected from Group I consisting of sulfuric acid and C1 to C6 alkanesulfonic acids optionally substituted with halogen; and step C of obtaining a compound of formula (2-c) by reducing the compound of formula (2-b) obtained in step B in the presence of a heterogeneous transition metal catalyst;

wherein the compound of formula (2-a) obtained in step A is subjected to step B without isolation.

3. The production method according to claim 2, wherein the heterogeneous transition metal catalyst is a heterogeneous platinum catalyst.

* * * * *